United States Patent

Ransohoff

[11] Patent Number: 5,242,586
[45] Date of Patent: Sep. 7, 1993

[54] COLUMN PROTECTION SYSTEM FOR LIQUID CHROMATOGRAPHY SYSTEM

[75] Inventor: Thomas C. Ransohoff, Fairfield, Conn.

[73] Assignee: Biotage Inc., Charlottesville, Va.

[21] Appl. No.: 628,826

[22] Filed: Dec. 17, 1990

[51] Int. Cl.⁵ .............................. B01D 15/08
[52] U.S. Cl. ...................... 210/198.2; 73/61.52; 73/61.56; 73/61.57; 210/85; 210/90; 210/103; 210/134; 210/143; 210/656
[58] Field of Search ........... 210/198.2, 672, 659, 210/143, 139, 87, 90, 85, 143, 134, 136, 149, 739, 321.72, 321.65, 96.1, 103, 656; 73/61.10, 61.1 C, 61.52, 61.53, 61.56, 61.57; 364/497, 502; 422/70

[56] References Cited

U.S. PATENT DOCUMENTS

| | | | |
|---|---|---|---|
| 4,116,046 | 9/1978 | Stein | 73/61.1 C |
| 4,117,727 | 10/1978 | Friswell et al. | 73/61.1 C |
| 4,153,554 | 5/1979 | von der Heide et al. | 210/96.2 |
| 4,840,730 | 6/1989 | Saxena | 210/96.1 |
| 4,897,184 | 1/1990 | Shouldice et al. | 210/87 |
| 4,911,703 | 3/1990 | Lysaght et al. | 604/28 |
| 5,112,492 | 5/1992 | Ransohoff | 210/198.2 |

Primary Examiner—Robert A. Dawson
Assistant Examiner—Sun Uk Kim
Attorney, Agent, or Firm—Sheldon H. Parker

[57] ABSTRACT

A liquid chromatography column protection system having a system pump, a bubble trap, and a column includes detectors for monitoring certain system conditions such as the presence of air or overpressurization and valves and controlling means for shutting down system operation when the conditions are detected.

3 Claims, 2 Drawing Sheets

COLUMN PROTECTION SYSTEM FOR LIQUID CHROMATOGRAPHY SYSTEM

BACKGROUND OF THE INVENTION

This invention is directed to liquid chromatography and is particularly concerned with protection of the liquid chromatography system during unattended operation from the presence of air and overpressure.

In liquid chromatography a liquid sample is passed by a flowing stream of liquid solvent or buffer (the mobile phase) through a column packed with particulate matter (the stationery phase). While passing through the column the various components in the sample separate from one another by adsorbing and desorbing from the stationery phase at different rates such that these individual components elute from the column at different times. The separated components then flow through a detector which responds to each component both qualitatively and quantitatively, providing the user with the ability to achieve a separation and therefore to purify one or more of the constituents of the sample.

In liquid chromatography it is important to protect the particulate matter or chromatography media from overpressurization especially where the media is a gel. Overpressurization will crush the media which will lose its ability to process the liquid sample.

Additionally it is important to prevent air from entering the chromatography column because air will interfere with the liquid sample from reaching active sites in the chromatography media. The presence of air establishes air pockets within the column blocking even flow of the liquid sample through the column. Accordingly overpressurization and the presence of air substantially interfere with proper resolution of a liquid sample in the chromatography system and therefore will increase the cost of purifying the sample.

Similarly, other critical conditions may arise that threaten the continued performance of the chromatography column or the constituents of the fluid passing through it. These conditions include, but are not necessarily limited to, conditions of temperature, pH or conductivity.

SUMMARY OF THE INVENTION

The present invention provides a column protection system which facilitates the unattended operation of a liquid chromatography system and which will close down the system in the event air, overpressurization or any other detectable critical condition occur in a system threatening the integrity of the chromatography media in the column or the constitutents of the fluid mixture passing through the column.

In accordance with the present invention the liquid chromatography system is provided with a feed pump, column inlet and outlet valves, a bubble trap, a bubble detector, a pressure sensor, and any other required detectors, for example, pH, conductivity, or temperature detection for monitoring online conditions and for interrupting flow to and from a liquid chromatography column in the event these critical and normally undesired conditions are encountered.

OBJECT OF THE INVENTION

It is an object of the invention to provide column protection system which arrests system operation in the event air, system overpressurization, or other detectable critical conditions occur.

Other and further objects of the invention will occur to one skilled in the art upon employment of the invention in practice or will become apparent on an understanding of the following detailed description.

DESCRIPTION OF THE DRAWING

A preferred embodiment of the invention has been selected for purposes of description and illustration and is shown in the accompanying drawing in which.

Figure 1:
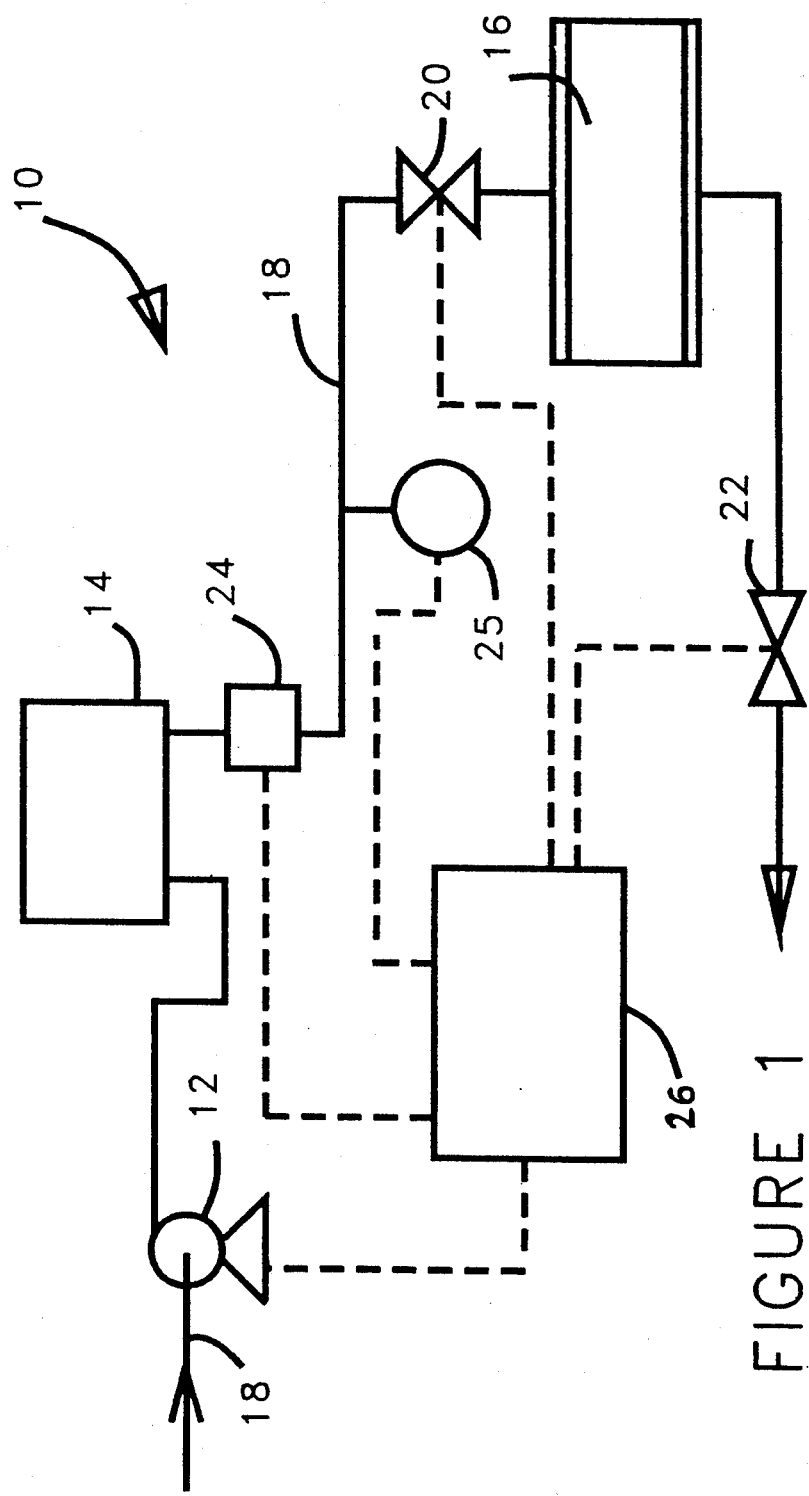
FIG. 1 is a schematic of the column protection system, as used in a liquid chromatography system.

Referring now to the drawing, FIG. 1, a protection system 10 is for a liquid chromatography system having a feed pump 12, a bubble trap 14, and a chromatography column 16. A liquid flow line 18 conducts liquid to and from pump 12, into and out of the bubble trap 14, into and out of the column via inlet valve 20 and outlet valve 22. The outlet 18 from the column is to detectors and fraction collector (not shown) for sorting out the constituents of the liquid sample.

A bubble detector 24 operating, for example, on optical, ultrasonic or capacitance sensing principles, is located in the liquid flow line at the outlet of the bubble trap for the purpose of detecting the presence of air at the inlet of the column. The system also includes a pressure switch 25 set to the desired pressure limit of the column—typically in the range of 2 psi to 200 psi, but in some cases substantially higher, e.g., up to 2000 psi. In addition, other monitors that indicate a critical condition via a contact closure may be connected to the sysem. In the event that the pressure should reach the pressure limit, air is detected by the bubble detector, or another critical condition is detected, the column protection system including a controller 26 will shut down the pump 12, close the inlet and outlet valves 20, 22 and indicate the alarm and its nature via a horn 28, lights 30 or other suitable indicators shown in FIG. 2.

Recovery is achieved by bypassing the alarm/shutdown mode of operation of the column protection system until normal system operation is restored at which time the system is reset to perform its watch dog function.

The system may also include an adjustable timer 32 (FIG. 2) to screen out transient conditions of air presence or overpressurization. For example, the timer may be set to require the presence of air or pressurization to endure at least two to three seconds before shutdown.

The system is also capable of monitoring the system for other conditions during operation. For example, periodic cleaning or sanitization of the chromatography system is often required. Sanitization is frequently achieved using a cleaning solution such as 1.0N sodium hydroxide. This can be done using the protection system over night or over a weekend utilizing a pH or conductivity detector at the column outlet. In this embodiment, the system will shut down when a pH/conductivity reading indicates that the column has been saturated with the cleaning solution. When this condition is achieved, the monitoring system will shut off a column and close down the system's pump, thereby conserving cleaning solution.

In another use of the system according to the present invention, a dry line condition can be detected so that when cleaning (sanitizing) or equilibrating the system with a buffer such as sodium phosphate for maintaining a constant pH, level the system will be shut down by a suitable flow detector to prevent the supply tank running dry.

Figure 2:
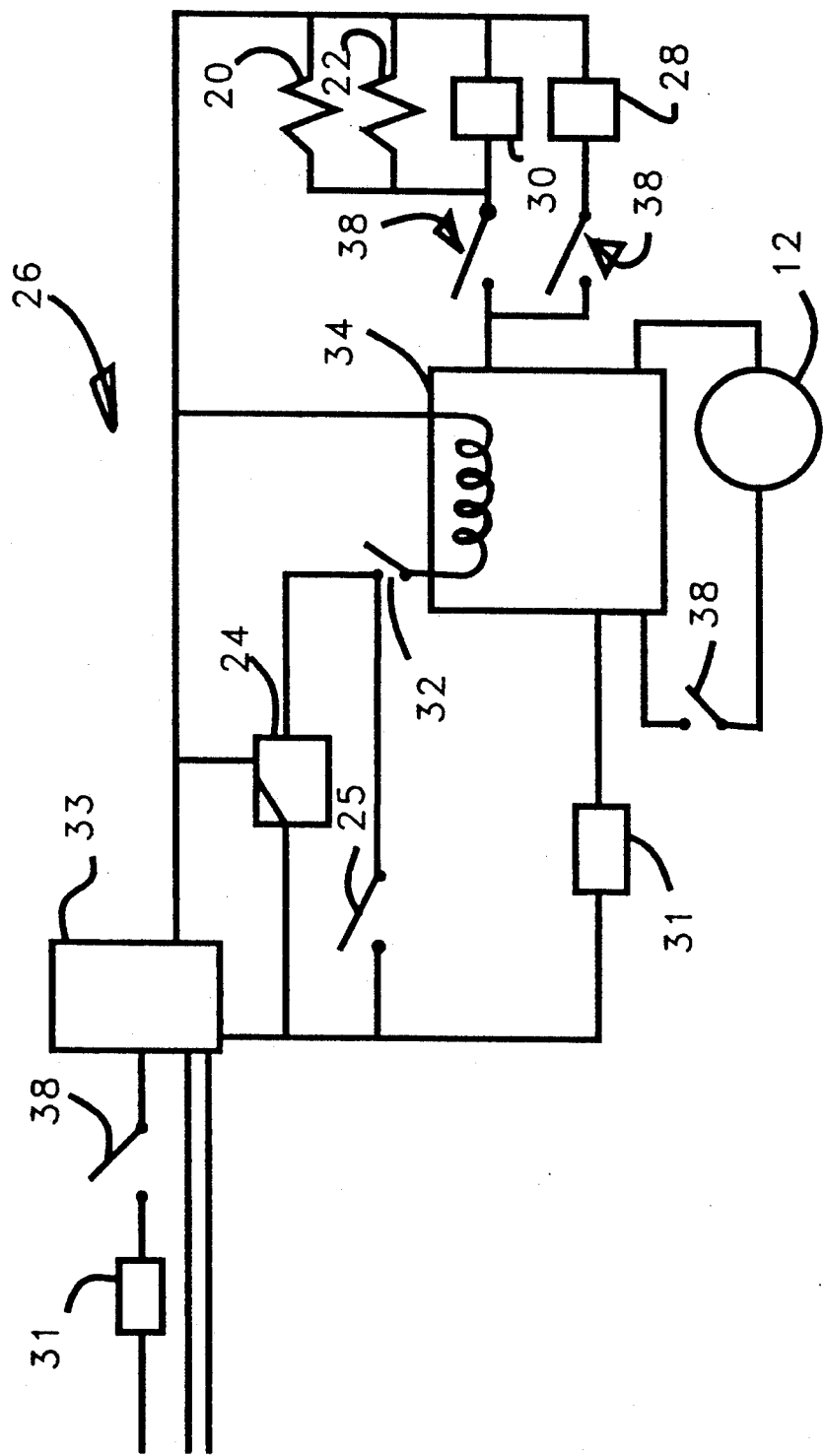
FIG. 2 is an electrical schematic.

It will be therefore seen from the electrical schematic of FIG. 2 that a representative column protection system includes fuses 31 control relays 34, a bubble detector 24, pressure sensitive switch 25 and switches 38 for operating the pump for actuating the inlet 20 and outlet 22 valves and for emitting warning signals such as an alarm horn 28 or alarm lights 30, and may additionally include a power supply 33 for operating the system at 12-24 volts D.C., detectors or sensors for other key or critical operating parameters or other means for signalling alarm conditions.

Having thus described the invention, I claim:

1. A liquid chromatography column protection system comprising a system pump for supplying liquid via a supply line, a chromatography column for receiving the liquid, a bubble trap intermediate the pump and column for removing air from the system, a bubble detector for detecting the presence of air in the supply ahead of the column, a pressure detector for detecting overpressurization of the liquid supply to the column, inlet and outlet valves for the column, and control means for monitoring the bubble detector and the pressure detector, for arresting system operation by shutting down the system pump and shutting the inlet and outlet valves when undesired conditions are detected, and for restoring normal system operation after shutdown.

2. A liquid chromatography column protection system as defined in claim 1 which further includes a pH or conductivity detector for shutting down a sanitizing equilibrating operation when system conditions reach a predetermined end point of sanitization or equilibrium of the chromatography column.

3. A liquid chromatography column protection system as defined in claim 1 which further includes a temperature detector for shutting down a system operation when system conditions reach a predetermined temperature.

* * * * *